United States Patent
Hassan et al.

(10) Patent No.: US 9,566,356 B2
(45) Date of Patent: Feb. 14, 2017

(54) STERILIZING DEVICE AND STERILIZATION METHOD HAVING ENERGY RECOVERY

(71) Applicant: Robert Bosch GmbH, Stuttgart (DE)

(72) Inventors: Mahmoud Hassan, Vienna (AT); Wilfried Grabner, Ternitz (AT); Erich Gyoeroeg, Bad Tatzmannsdorf (AT)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/766,548

(22) PCT Filed: Jan. 3, 2014

(86) PCT No.: PCT/EP2014/050033
§ 371 (c)(1),
(2) Date: Aug. 7, 2015

(87) PCT Pub. No.: WO2014/121953
PCT Pub. Date: Aug. 14, 2014

(65) Prior Publication Data
US 2015/0374864 A1    Dec. 31, 2015

(30) Foreign Application Priority Data

Feb. 11, 2013 (DE) .......... 10 2013 202 188

(51) Int. Cl.
*A61L 2/08* (2006.01)
*A61L 2/00* (2006.01)
(Continued)

(52) U.S. Cl.
CPC .. *A61L 2/07* (2013.01); *A61L 2/04* (2013.01); *F28D 20/0039* (2013.01)

(58) Field of Classification Search
CPC ..................................... A61L 2/00; A23L 3/00
(Continued)

(56) References Cited

U.S. PATENT DOCUMENTS

| | | | | |
|---|---|---|---|---|
| 4,708,849 A | * | 11/1987 | Mielnik, Jr. .............. | A23L 3/10 122/406.1 |
| 5,787,720 A | | 8/1998 | Lenz et al. | |
| 2011/0033585 A1 | | 2/2011 | Wasmuht et al. | |

FOREIGN PATENT DOCUMENTS

| DE | 4312474 | 11/1994 |
|---|---|---|
| DE | 4442709 | 6/1996 |

(Continued)

OTHER PUBLICATIONS

International Search Report for Application No. PCT/EP2014/050033 dated Mar. 13, 2014 (English Translation, 2 pages).

*Primary Examiner* — Monzer R Chorbaji
(74) *Attorney, Agent, or Firm* — Michael Best & Friedrich LLP

(57) ABSTRACT

The present invention relates to a sterilizing device (1), comprising at least one chamber (2) for sterilizing products (4), a primary fluid circuit (3) connected to the chamber (2) for providing hot water and/or hot steam to the chamber, a secondary fluid circuit (8) for heating and/or cooling the primary fluid circuit (3), wherein the secondary fluid circuit (8) is connected to the primary fluid circuit (3) by means of a second heat exchanger (5), and a stratified storage tank (11) in the secondary fluid circuit (8) having a plurality of temperature zones (12), wherein the temperature zones (12) can be separately charged with and discharged of the fluid of the secondary fluid circuit (8).

19 Claims, 1 Drawing Sheet

(51) Int. Cl.
*A61L 2/07* (2006.01)
*A61L 2/04* (2006.01)
*F28D 20/00* (2006.01)

(58) Field of Classification Search
USPC .................................. 422/1, 26, 38, 307
See application file for complete search history.

(56) References Cited

FOREIGN PATENT DOCUMENTS

| | | |
|---|---|---|
| DE | 102007054429 | 5/2009 |
| DE | 102010060919 | 6/2012 |
| EP | 724014 | 7/1996 |
| EP | 2289615 | 3/2011 |
| EP | 2455696 | 5/2012 |

* cited by examiner

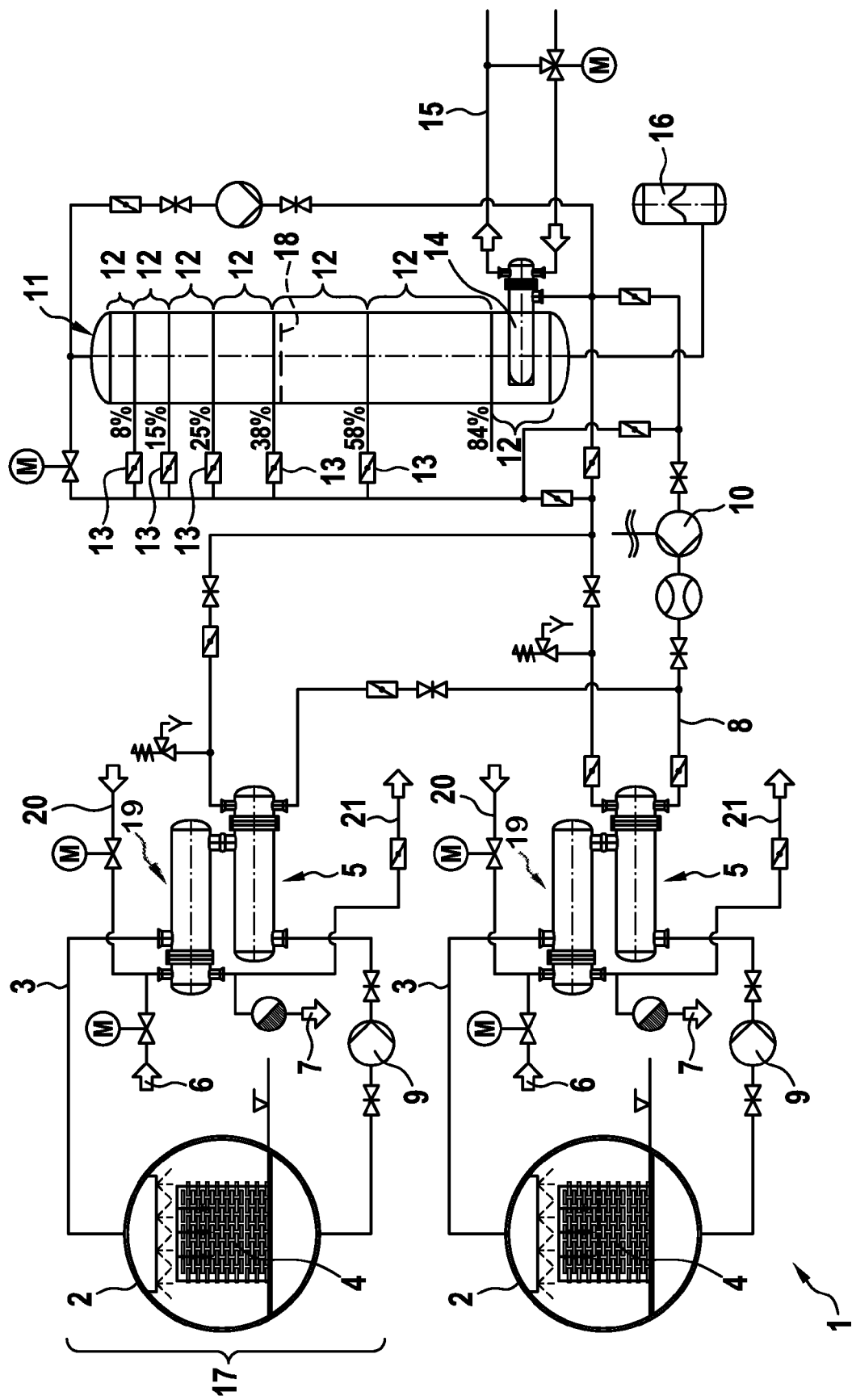

STERILIZING DEVICE AND STERILIZATION METHOD HAVING ENERGY RECOVERY

BACKGROUND OF THE INVENTION

The present invention relates to a device and a method for sterilizing products with hot water and/or hot steam.

The terminal sterilization, in particular hot water spraying, is generally carried out on a relatively large scale, for example with volumes of over 5 m$^3$, in order to be able to sterilize a quantity of products per run which is as large as possible. The run time can be influenced by means of the quantity of available media, the size of the heat exchangers and the obtainable temperature of the heating or cooling media. The design of these components is in turn not only dependent on the loading density, the product and the required process time but also on the size and mass of the sterilizer which has to be consecutively heated or cooled. A very large energy consumption is associated with the continuous cooling and heating of the sterilizing device.

SUMMARY OF THE INVENTION

It is possible to significantly reduce the energy consumption for sterilizing products using the sterilizing device according to the invention and the sterilization method according to the invention. Energy savings up to 40% are possible when heating the fluid for the chamber for the sterilization process and up to 60% when cooling said fluid. This is achieved by a sterilizing device comprising at least one chamber for sterilizing products and a primary fluid circuit connected to the chamber. The primary fluid circuit is used to provide hot water and/or hot steam to the chamber or, respectively, the products. In addition, the sterilizing device comprises a secondary fluid circuit and a second heat exchanger. The secondary fluid circuit is connected to the primary fluid circuit by means of the second heat exchanger; thus enabling the primary fluid circuit to be heated and/or cooled by means of the second fluid circuit. The sterilizing device further comprises a stratified storage tank in the secondary fluid circuit. The stratified storage tank comprises a plurality of temperature zones, wherein the individual temperature zones can be separately charged with and discharged of the fluid of the secondary fluid circuit. In order to cool the primary fluid circuit, heat is therefore removed from said primary fluid circuit by means of the second heat exchanger. In so doing, a warming of the fluid in the secondary fluid circuit occurs. This heat can be stored in the temperature zones of the stratified storage tank. During the subsequent heating of the fluid in the primary fluid circuit, the heat is removed from the stratified storage tank and transmitted via the second heat exchanger to the primary fluid circuit. The individual temperature zones of the stratified storage tank enable fluid to be held available at different temperatures. The primary fluid circuit is supported by a mixing of the fluid from the individual temperature zones or by removing said fluid in a stratified manner from the individual temperature zones in order to be heated or cooled to the desired temperature. The primary fluid circuit preferably comprises a first heat exchanger. The first heat exchanger is connected to an independent heating or cooling line; thus enabling the primary fluid circuit to also be operated independently of the second fluid circuit. The energy consumption of the sterilizing device can be significantly reduced by the use of the stratified storage tank according to the invention.

Provision is preferably made for a third heat exchanger. Said third heat exchanger is used to additionally cool the fluid in the secondary fluid circuit, wherein the third heat exchanger is connected to an external cooling circuit.

Provision is particularly made for the third heat exchanger to be integrated into the stratified storage tank. In particular, the third heat exchanger is thereby installed in the temperature zone having the lowest temperature, i.e. particularly in the lowest temperature zone. It is possible by means of the integrated third heat exchanger to cool the fluid directly in the stratified storage tank and/or when said fluid is flowing out of the stratified storage tank in order thereby to increase the efficiency of the energy savings during the cooling process.

The stratified storage tank comprises respectively one separate, controllable connection to the temperature zones. The individual temperature zones can be directly charged with and discharged of fluid via this controllable connection. The controllable connections are thus used during the removal of fluid from the stratified storage tank for the mixing of fluid to achieve the desired temperature or for removing said fluid in a stratified manner. When charging the stratified storage tank, the fluid is guided via the controllable connections into the correct temperature zone.

The stratified storage tank is particularly designed to accommodate a fluid column. In so doing, the different temperature zones are disposed on top of one another or adjacent to one another.

In order to prevent the fluid of different temperature zones from mixing to the greatest possible extent, separators are provided in the stratified storage tank. The separators do not necessarily have to completely separate the temperature zones from one another. The separators are primarily used to prevent a turbulent mixing of the fluid of different temperature zones.

The stratified storage tank comprises at least three, preferably at least four temperature zones which can be separately charged with and discharged of fluid.

By means of the secondary fluid circuit comprising a stratified storage tank, a plurality of chambers can also be supplied with respectively one primary fluid circuit in a preferable manner. In so doing, a second heat exchanger, which is connected to the secondary fluid circuit, is provided per primary fluid circuit.

A control device is furthermore preferably provided, which controls the volume flow in the individual fluid lines, in particular in the connections of the stratified storage tank, in an open or closed loop.

The invention furthermore comprises a sterilization method comprising the following steps: (i.) sterilizing of products in a chamber with hot water and/or hot steam from a primary fluid circuit, (ii) optional heating or cooling of the primary fluid circuit by means of a secondary fluid circuit, and (iii) storing of the fluid of the second fluid circuit in different temperature zones.

The advantageous embodiments of the sterilizing device according to the invention can correspondingly be advantageously applied to the sterilization method according to the invention.

Provision is preferably made for the fluid of the secondary fluid circuit to be mixed from the different temperature zones or to be removed in a stratified manner. Accordingly, provision is also preferably made for a return flow coming from the second heat exchanger to be correspondingly divided up over the different temperature zones.

Provision is furthermore preferably made for the stored fluid, preferably in the temperature zone having the lowest temperature, to be able to be additionally cooled by means of a cooling circuit.

BRIEF DESCRIPTION OF THE DRAWINGS

An exemplary embodiment of the invention is described below in detail with reference to the accompanying drawing. In the drawing:

FIG. 1 shows a circuit diagram of an inventive sterilizing device according to one exemplary embodiment.

DETAILED DESCRIPTION

FIG. 1 shows a circuit diagram of a sterilizing device 1 according to the exemplary embodiment. The sterilizing device 1 comprises a chamber 2. Products to be sterilized are disposed in this chamber 2. The chamber 2 is connected to a primary fluid circuit 3. In said primary fluid circuit 3, the fluid is conveyed by means of a first pump 9 and heated or cooled down by means of a heat exchanger 19. The products 4 in the chamber are sprayed with hot water by means of the primary fluid circuit 3. A steam inlet 6, a cooling medium supply line 20, a cooling medium return line 21 and a condensate drain 7 are configured at the first heat exchanger 19.

A second heat exchanger 5 is furthermore provided. The second heat exchanger 5 connects the primary fluid circuit 3 to a secondary fluid circuit 8. The secondary fluid circuit 8 is used to heat and cool the primary fluid circuit 3. This heat exchange takes place across the second heat exchanger 5.

The fluid, preferably water, in the secondary fluid circuit 8 is conveyed by means of a second pump 10. Said pump can be individually regulated as to the output thereof.

The secondary fluid circuit 8 further comprises a stratified storage tank 11. A fluid column, which is subdivided into different temperature zones that are disposed on top of one another or adjacent to one another, is situated in said stratified storage tank 11. Individual connections 13 lead to the temperature zones 12. The individual temperature zones 12 of the stratified storage tank 11 can be charged with and discharged of fluid via said connections 13. To this end, the connections 13 comprise check valves or mixing valves which can be controlled via a control device in an open or closed loop.

In addition, separators 18 are provided between the temperature zones 12, said separators preventing a turbulent mixing of the fluid in the stratified storage tank 11 to the greatest possible extent.

The fluid for the secondary fluid circuit 8 can be mixed to the appropriate temperature or removed in a stratified manner. As a result, it is possible to heat and cool down the primary fluid circuit 3 in a targeted manner via the second heat exchanger 5.

A third heat exchanger 14 is provided for an additional cooling of the secondary fluid circuit 8. The third heat exchanger 14 is integrated into the stratified storage tank 11, in particular into the lowest temperature zone 12. The third heat exchanger 14 is connected to an external cooling circuit 15.

A pressure compensation device 16 is furthermore provided in the secondary fluid circuit 8.

The illustration in FIG. 1 shows a further arrangement 17 which likewise comprises a primary fluid circuit 3, a chamber 2 and a first heat exchanger 19. A plurality of these further arrangements 17 can be connected to the secondary fluid circuit 8.

A heating device, for example a boiler for additionally heating up the secondary fluid circuit 8 is not shown in FIG. 1. The full energy for heating the chamber 2 is required in the first sterilization cycle. The water temperature in the primary fluid circuit is approximately 121° C. in the sterilization phase.

The stratified storage tank 11 is always filled with the fluid of the second fluid circuit 8, in particular with water, wherein the temperature of the fluid rises from bottom to top. The separators 18 in the stratified storage tank 11 prevent a rapid mixing of the individual temperature zones.

At the start of the cooling process for cooling the primary fluid circuit 3, the fluid of the secondary fluid circuit 8 is heated by the hot process water in the primary fluid circuit 3. The energy from the primary fluid circuit 3 is therefore transmitted via the second heat exchanger 5 to the secondary fluid circuit 8 and can be stored in the stratified storage tank 11. The hot fluid in the secondary fluid circuit 8 is loaded as a function of the temperature into the stratified storage tank 11 beginning at the top via the different connections 13.

In addition, the lowest temperature zone 12 is cooled with the third heat exchanger 14. This serves to ensure that the fluid circuit 13 is cooled down as quickly as possible.

During the next run of the method, i.e. during the next heating of the chamber 2, the hot fluid is removed in a stratified manner from the stratified storage tank 11. This occurs in a stratified manner until a positive energy input into the primary fluid circuit 3 can no longer be performed. From this point in time, the primary fluid circuit 3 is further heated via the steam line 6 until the target temperature is achieved.

The degree of efficiency is higher during the cooling process because the third heat exchanger 14 in the stratified storage tank 11 operates additionally in a supporting manner. The energy expenditure for the third heat exchanger 14 is lower than the energy expenditure during the conventional cooling process. The option exists to perform the cooling process only via the third heat exchanger 14 and the stratified storage tank 11 or additionally via the cooling medium supply line 20, which has the advantage, in the event of a failure of one of the systems, of being able to change to the other system. In the conventional process, the entire energy is removed via a cooling water system, usually a closed cooling circuit, from the primary fluid circuit 3. The cooling water system is itself cooled in turn via cooling units or cooling towers. By saving on cooling energy, the investment into the cooling system provided by the customer can on the one hand be less; and on the other hand, the running costs are also correspondingly lower.

The sterilizing device 1 shown here as well as the associated sterilization method can be used for a wide variety of chambers 2. An intelligent control system will ensure that the stratified storage tank 11 is always full. If fluid is removed from one temperature zone 12, fluid is simultaneously pumped into another temperature zone 12 so that the total volume in the stratified storage tank 11 remains the same. To this end, an intelligent control of the processes preferably takes place by means of controllable valves and temperature sensors in the piping, in the stratified storage tank 11, in the heat exchangers 5, 14, 19 and/or in the chamber 2.

What is claimed is:

1. A sterilizing device (1) comprising:
    at least one chamber (2) for sterilizing products (4),
    a primary fluid circuit (3) connected to the chamber (2) for providing hot water and/or hot steam to the chamber,
    a secondary fluid circuit (8) for heating and/or cooling the primary fluid circuit (3), wherein the secondary fluid circuit (8) is connected to the primary fluid circuit (3) by a secondary circuit heat exchanger (5), and
    a stratified storage tank (11) in the secondary fluid circuit (8) having a plurality of temperature zones (12), wherein the sterilizing device (1) includes an individual controllable connection (13) for each of the plurality of temperature zones (12), and wherein each controllable connection (13) separately charges a respective temperature zone (12) with the fluid of the secondary fluid circuit (8) and separately discharges the fluid of the secondary fluid circuit (8) from the respective temperature zone (12).

2. The sterilizing device according to claim 1, characterized by an additional heat exchanger (14) for cooling the fluid in the secondary fluid circuit (8), wherein the additional heat exchanger (14) is connected to a cooling circuit (15).

3. The sterilizing device according to claim 2, characterized in that the additional heat exchanger (14) is integrated into the stratified storage tank (11).

4. The sterilizing device according to claim 2, characterized in that the additional heat exchanger (14) is integrated into the temperature zone (12) having the lowest temperature.

5. The sterilizing device according to claim 1, characterized in that the stratified storage tank (11) is configured to accommodate a fluid column, wherein the temperature zones (12) are disposed on top of one another or adjacent to one another in the fluid column.

6. The sterilizing device according to claim 5, characterized in that at least one separator (18) is disposed in the stratified storage tank (11) in order to prevent a turbulent mixing of the fluid of different temperature zones (12).

7. The sterilizing device according to claim 1, characterized in that the stratified storage tank (11) comprises at least three temperature zones (12) which are separately charged with and discharged of fluid.

8. The sterilizing device according to claim 1, characterized in that the stratified storage tank (11) comprises at least four temperature zones (12) which are separately charged with and discharged of fluid.

9. The sterilizing device (1) according to claim 1, wherein each controllable connection (13) includes a valve controlled by a control device.

10. The sterilizing device (1) according to claim 9, wherein the valve is a check valve.

11. The sterilizing device (1) according to claim 10, wherein the control device controls the valve in an open loop.

12. The sterilizing device (1) according to claim 9, wherein the valve is a mixing valve.

13. The sterilizing device (1) according to claim 9, wherein the control device controls the valve in a closed loop.

14. A sterilization method comprising the following steps:
    sterilizing products (4) in a chamber (2) with hot water and/or hot steam from a primary fluid circuit (3),
    heating or cooling the primary fluid circuit (3) by means of a secondary fluid circuit (8),
    storing the fluid of the secondary fluid circuit (8) in different temperature zones (12) of a stratified storage tank (11), and
    separately charging a respective one of the plurality of temperature zones (12) with the fluid of the secondary fluid circuit (8) and separately discharging the fluid of the secondary fluid circuit (8) from the respective one of the plurality of temperature zones (12) via an individual controllable connection (13) for each of the plurality of temperature zones (12).

15. The sterilization method according to claim 14, characterized in that the fluid of the secondary fluid circuit (8) is mixed and/or removed in a stratified manner from the different temperature zones (12) in order to heat and/or cool the primary fluid circuit (3).

16. The sterilization method according to claim 14, characterized in that the stored fluid is cooled by means of a cooling circuit (15).

17. The sterilization method according to claim 14, characterized in that the stored fluid, in the temperature zone (12) having the lowest temperature, is cooled by means of a cooling circuit (15).

18. The sterilizing method according to claim 14, wherein the method is performed by a sterilizing device (1) including
    the chamber (2) for sterilizing the products (4),
    the primary fluid circuit (3) connected to the chamber (2) for providing hot water and/or hot steam to the chamber (2),
    the secondary fluid circuit (8) for heating and/or cooling the primary fluid circuit (3), wherein the secondary fluid circuit (8) is connected to the primary fluid circuit (3) by a secondary circuit heat exchanger (5), and
    the stratified storage tank (11) in the secondary fluid circuit (8), wherein the sterilizing device (1) includes the individual controllable connection (13) for each of the plurality of temperature zones (12), and wherein each controllable connection (13) separately charges a respective temperature zone (12) with the fluid of the secondary fluid circuit (8) and separately discharges the fluid of the secondary fluid circuit (8) from the respective temperature zone (12).

19. The sterilizing method according to claim 14 further comprising:
    controlling, via a control device, a valve of a respective controllable connection (13) for separately charging a respective temperature zone (12) with the fluid of the secondary fluid circuit (8) and separately discharging the respective temperature zone (12) with the fluid of the secondary cooling circuit (8).

* * * * *